United States Patent [19]

Torii et al.

[11] Patent Number: 4,604,457

[45] Date of Patent: Aug. 5, 1986

[54] 2-SUBSTITUTED CEPHEM DERIVATIVES AND PROCESS FOR PREPARING THE SAME

[75] Inventors: Shigeru Torii; Hideo Tanaka; Junzo Nogami, all of Okayama; Michio Sasaoka, Tokushima; Norio Saito, Tokushima; Takashi Shiroi, Tokushima, all of Japan

[73] Assignee: Otsuka Kagaku Kabushiki Kaisha, Osaka, Japan

[21] Appl. No.: 614,162

[22] PCT Filed: Sep. 6, 1983

[86] PCT No.: PCT/JP83/00299

§ 371 Date: May 8, 1984

§ 102(e) Date: May 8, 1984

[87] PCT Pub. No.: WO84/00965

PCT Pub. Date: Mar. 15, 1984

[30] Foreign Application Priority Data

Sep. 9, 1982 [JP] Japan ................. 57-157581

[51] Int. Cl.$^4$ ........................... C07D 501/22
[52] U.S. Cl. ................... 540/223; 540/229; 540/230
[58] Field of Search .............. 544/23, 29, 30

[56] References Cited

U.S. PATENT DOCUMENTS 3,639,396  2/1972  Bickel et al. ............ 544/29
3,968,109  7/1976  Koster et al. ........... 544/29
4,098,999  7/1978  Dolfini et al. .......... 544/23
4,416,879  11/1983 Takaya et al. .......... 544/29
4,482,551  11/1984 Furlenmeier et al. ..... 544/27

FOREIGN PATENT DOCUMENTS 9084690  9/1972  Japan ................... 544/29
9016896  1/1984  Japan ................... 544/29

OTHER PUBLICATIONS

Balsamo et al., "Chemistry of Dihydrothiazine Ring Moiety of Cephalosporins . . . ", *J. Org. Chem.* 41: 2150-2153 (1976).
Spry et al., "2-Alkoxycephalosporins, . . . ", *Chem. Abst.* 80: 95975K (1974).

Primary Examiner—Mark L. Berch
Assistant Examiner—G. Hendricks
Attorney, Agent, or Firm—Armstrong, Nikaido, Marmelstein & Kubovcik

[57] ABSTRACT

A 2-substituted cephem derivative represented by the formula

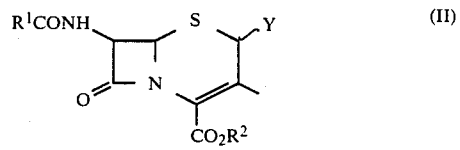

wherein $R^1$ represents a substituted or unsubstituted phenyl group, substituted or unsubstituted phenylmethyl group or substituted or unsubstituted phenoxymethyl group, $R^2$ represents hydrogen atom or protective group for carboxylic acid and Y represents allyloxy group, benzyloxy group, alkylthio group, carboxyalkylthio group or group of the formula

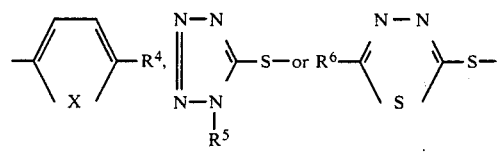

wherein $R^4$ represents hydrogen atom or lower alkyl group, X represents —O—, —S— or

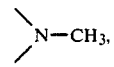

$R^5$ represents hydrogen atom, a lower alkyl group or phenyl group and $R^6$ represents hydrogen atom or lower alkyl group, and a process for preparing the derivatives.

3 Claims, No Drawings

2-SUBSTITUTED CEPHEM DERIVATIVES AND PROCESS FOR PREPARING THE SAME

TECHNICAL FIELD AND DISCLOSURE OF INVENTION

This invention relates to novel 2-substituted cephem derivatives and to a process for the preparation of the same. More specifically stated, the present invention provides 2-substituted cephem derivatives represented by the formula

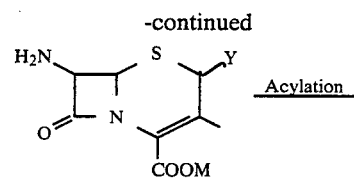

wherein $R^1$ represents substituted or unsubstituted phenyl group, substituted or unsubstituted phenylmethyl group or substituted or unsubstituted phenoxymethyl group, $R^2$ represents hydrogen atom or protective group for carboxylic acid and Y represents alkoxy group, allyloxy group, benzyloxy group, alkylthio group, carboxyalkylthio group or group of the formula

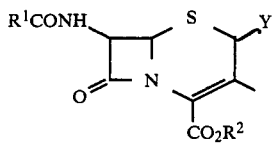

wherein $R^4$ represents hydrogen atom or lower alkyl group, X represents —O—, —S— or

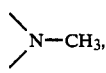

$R^5$ represents hydrogen atom, lower alkyl group or phenyl group and $R^6$ represents hydrogen atom or lower alkyl group, and a process for preparing the derivatives.

The 2-substituted cephem derivatives of the formula (II) are novel compounds undisclosed in literature and can be converted into useful compounds having an antibacterial activity by, for example, the saponification of the carboxylic acid-protecting group or acyl exchange at the amido site in the 7-position. For example, the compound (II) can be converted into a compound of the formula (X) which is useful as the antibacterial agent, according to the following reaction equation.

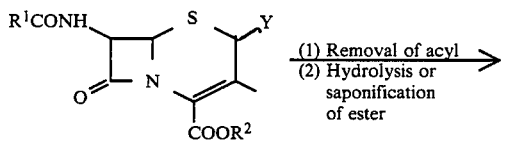

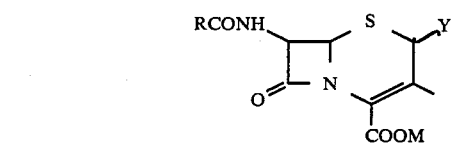

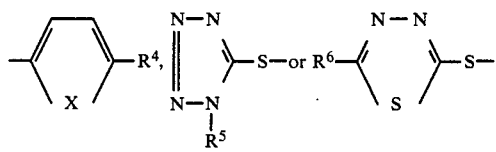

In the above reaction equation, $R^1$, $R^2$ and Y are as defined above, M represents hydrogen atom or alkali metal and R represents a group such as that of

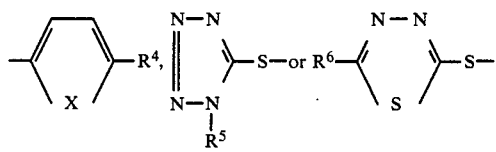

Examples of the substituted or unsubstituted phenyl groups represented by $R^1$ in the formula (II) are phenyl, phenyl substituted with lower alkyl, lower alkoxy, halogen, nitro or the like on the benzene nucleus such as p-methoxyphenyl, p-chlorophenyl, m-chlorophenyl, o-chlorophenyl, p-methylphenyl, p-nitrophenyl, etc. Exemplary of the substituted or unsubstituted phenylmethyl groups are phenylmethyl, phenylmethyl substituted with lower alkyl, lower alkoxy, halogen, nitro or the like on the benzene nucleus such as p-chlorophenylmethyl, p-nitrophenylmethyl, p-methylphenylmethyl, etc. Representative of the substituted or unsubstituted phenoxymethyl groups are phenoxymethyl, phenoxymethyl substituted with lower alkyl, lower alkoxy, halogen, nitro or the like on the benzene nucleus such as p-chlorophenoxymethyl, etc.

Examples of the carboxylic acid-protecting groups represented by $R^2$ are alkyl, halogenated alkyl, methyl substituted with phenyl optionally substituted and like protective groups commonly used. Preferred examples of the alkyl groups are those having 1 to about 4 carbon atoms such as methyl, tert-butyl, etc. Preferable halogenated alkyl groups are lower alkyl groups having 1 to about 4 carbon atoms and substituted with at least one halogen group such as 2,2,2-trichloroethyl, etc. Preferred methyl groups substituted with phenyl optionally substituted are benzyl, p-nitrophenylmethyl, diphenylmethyl, etc.

Examples of the alkoxy groups represented by Y are lower alkoxy groups having 1 to about 4 carbon atoms such as methoxy, ethoxy, etc. Representative of the alkylthio groups are lower alkylthio groups having 1 to about 4 carbon atoms such as methylthio, ethylthio, butylthio, isobutylthio, etc. Illustrative of the carboxyalkylthio groups are carboxy lower alkylthio groups having about 2 to about 4 carbon atoms such as —SCH$_2$COOH, —SCH$_2$CH$_2$COOH, —SCH$_2$CH$_2$CH$_2$COOH, etc. Exemplary of the groups

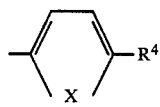

are furanyl, 2-methylfuranyl, thiophene-2-yl, 2-methylthiophene-5-yl, N-methylpyrrole-2-yl, etc. Representative of the groups

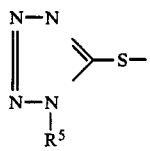

are 1,2,3,4-tetrazole-5-thio, 1-phenyl-1,2,3,4-tetrazole-5-thio, 1-methyl-1,2,3,4-tetrazole-5-thio, etc. Illustrative of the groups

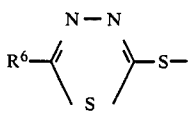

are 1,3,4-thiadiazole-5-thio, 2-methyl-1,3,4-thiadiazole-5-thio, etc.

The compound (II) can be prepared by reacting a cephem derivative of the formula

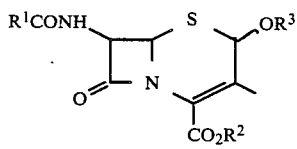

wherein $R^1$ and $R^2$ are as defined above and $R^3$ represents lower alkyl group or lower alkylcarbonyl group with a nucleophilic reagent of the formula

Y−H wherein Y is as defined above in the presence of an acid or iodine. (When the compound (I) wherein $R^3$ is alkyl is used as the starting material, a nucleophilic reagent wherein Y is alkoxy is not usable.)

The cephem derivative (I) serving as the starting material wherein $R^3$ is lower alkyl can be prepared, for example, from a cephalosporin derivative of the formula

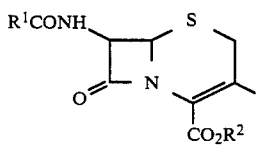

wherein $R^1$ and $R^2$ are as defined above by the processes disclosed in Tetrahedron Letters, 1978, 409 and 1972, 3717 or by a similar process. The cephem derivative (I) can be also produced by the electrolytic oxidation of the compound (A) in the presence of a primary of secondary alcohol or lower carboxylic acid and a supporting electrolyte. More specifically stated, useful primary or secondary alcohols are methanol, ethanol, n-propanol, n-butanol, isopropanol, isobutanol and like lower alcohols, and useful carboxylic acids are formic acid, acetic acid, propionic acid and the like. These compounds are used in an amount of about 5 to about 100 times the amount of the compound (A) serving as the starting material. Suitable supporting electrolytes include salts usable in usual electrolytic oxidation, such as ammonium formate, ammonium acetate, tetraethylammonium formate, tetraethylammonium acetate, tetrapropylammonium acetate, tetrabutylammonium acetate, tetrabutylammonium tosylate, tetraethylammonium tosylate, tetrabutylammonium perchlorate, triethylbenzylammonium chloride and like ammonium salts, salts of alkali metals or alkaline earth metals (such as salts of lithium, sodium, potassium, magnesium, calcium, barium or the like) of formic acid, acetic acid, propionic acid or like lower fatty acids, salts of alkali metals of perchloric acid or like perhalogenic acid, etc. When lower carboxylic acid is used as a solvent for the electrolytic oxidation, a metal salt of the lower carboxylic acid is preferably used. In this case, sodium hydroxide, potassium hydroxide, barium oxide, calcium oxide, magnesium oxide or the like may be incorporated in the reaction system to form a salt of the carboxylic acid. While the amount of the supporting electrolyte to be used varies with the kind of the electrode or the shape of electrolytic cell and other conditions, a preferred amount thereof is that sufficient to form a saturated solution. Usable as the electrodes is any of suitable electrodes commonly used in the art among which platinum or carbon electrode is preferably used. The electrolysis can be conducted at either controlled potential or constant voltage, for example at a constant current density in the range of 1 to 500 m $A/cm^2$, preferably 3 to 50 m $A/cm^2$. While the required quantity of electricity varies with the selection of the solvent and supporting electrolyte, electric current is passed through the electrolyte at usually 2 to 50 F., preferably 2 to 15 F., per mole of the compound (A). The temperature suitable for the electrolysis is adequately selected from the range of −10° to 60° C.

Useful nucleophilic reagents of the formula Y−H wherein Y is as defined above are methyl alcohol, ethyl alcohol and like lower alcohols, allyl alcohol, benzyl alcohol and the like; methanethiol, ethanethiol, butanethiol, isobutanethiol and like lower alkylthiols; furan, 2-lower alkylfuran, thiophene, 2-lower alkylthiophene, N-methylpyrrole and the like; 5-mercapto-1,2,3,4-tetrazole, 1-lower alkyl-5-mercapto-1,2,3,4-tetrazole, 1-phenyl-5-mercapto-1,2,3,4-tetrazole and the like; 5-mercapto-1,3,4-thiadiazole, 2-lower alkyl-5-mercapto-1,3,4-thiadiazole and the like; etc.

The nucleophilic reagent is employed in an amount of usually about 1 to about 50 moles, preferably about 1 to about 10 moles, per mole of the cephem derivative (I) to be used as the starting material. The nucleophilic reagent which is a liquid having a low viscosity such as lower alcohol, furan, methylfuran or the like can be used by itself as a solvent. When a nucleophilic reagent of the other type is used, the reaction is carried out by using an organic solvent inert to the reaction. Suitable examples of the organic solvent are methylene chloride, chloroform, carbon tetrachloride, 1,2-dichloroethane, chlorobenzene and like chlorinated hydrocarbons; ethyl acetate, ethyl formate, methyl formate and like esters of lower fatty acids; nitroethane, nitromethane and like nitro compounds; carbon disulfide; acetonitrile, butyronitril and like nitriles; etc. These solvents can be used singly or at least two of them are usable in admixture. The amount of the organic solvent to be used is not particularly limited but is such that the amount of the compound (I) is usually 0.1 to 50% (w/v), preferably 1 to 30% (w/v), based on the solvent.

In the present invention, the reaction between the cephem derivative (I) and the nucleophilic reagent is conducted in the presence of an acid or iodine. Useful acids include p-toluenesulfonic acid, methanesulfonic acid, trifluoroacetic acid and like organic acids; sulfuric acid, hydrochloric acid and like inorganic acids; aluminium chloride, tin chloride, titanium chloride, boron trifluoride and like Lewis acids; etc. Although variable depending on the kind of the catalyst and the nucleophilic reagent, etc., the amount of the catalyst to be used is usually about 0.01 to about 10 mole %, preferably about 0.1 to about 10 mole %, per mole of the compound (I). The reaction is performed at a temperature of usually about −60° to about 50° C., preferably −40° C. to room temperature and is completed usually in 10 minutes to 10 hours, although the reaction time varies with the reaction temperature and the kind of the catalyst and nucleophilic reagent.

The 2-substituted cephem derivative (II) thus obtained is separated from the reaction mixture and purified by the usual separation method such as column chromatography, recrystallization or the like.

The present invention will be described below in more detail with reference to the following Examples in which Ph stands for phenyl group; Ac for acetyl group; Et for ethyl group; and r.t. for room temperature.

EXAMPLE 1

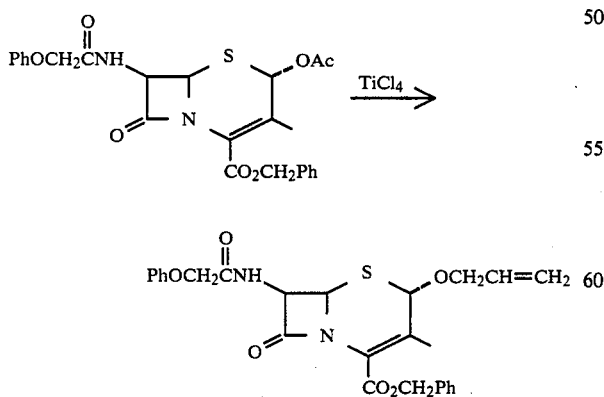

Dissolved in dry methylene chloride (2 ml) was benzyl ester of 2-acetoxy-7-phenoxyacetamido-3-desacetoxy cephalosporanic acid (130 mg, 0.26 mmol), and the solution was cooled to −25° C. Thereto added were allylalcohol (2 ml, 29.4 mmol) and then titanium tetrachloride (15 μl, 0.14 mmol). The reaction was carried out at temperatures gradually elevated from −25° C. to 3° C. while stirring the reaction mixture for 4.3 hours. A saturated aqueous solution of sodium hydrogen carbonate was added to the resulting reaction mixture whereupon the reaction was stopped. The reaction product was extracted with methylene chloride. The methylene chloride solution was washed with a saturated aqueous solution of sodium chloride, dried over anhydrous sodium sulfate and concentrated. The residue thus obtained was subjected to separation and purification by silica gel column chromatography using benzene-ethyl acetate (20:1), giving 108 mg of benzyl ester of 2-allyloxy-7-phenoxyacetamido-3-desacetoxy cephalosporanic acid in 83% yield.

IR (CHCl$_3$): 1782, 1772, 1690 cm$^{-1}$.

$^1$HNMR (CDCl$_3$, δ): 2.15 (s, 3H), 4.15 (m, 2H), 4.54 (s, 2H), 4.92 (s, 1H), 5.10 (d, 1H, 4.4 Hz), 5.28 (s, 2H), 5.0–5.5 (m, 3H), 5.94 (dd, 1H, 4.4 Hz, 8.8 Hz), 6.8–7.5 (m, 11H).

EXAMPLE 2

Allyl alcohol (2 ml, 29.4 mmol) was added to benzyl ester of 2-acetoxy-7-phenoxyacetamido-3-desacetoxy cephalosporanic acid (130 mg, 0.26 mmol) at room temperature to obtain a uniform solution. Iodine (2 mg) was added to the solution and the mixture was stirred for 4.7 hours. The reaction mixture was diluted with methylene chloride (30 ml) and the dilution was washed successively with 5% sodium thiosulfate and a saturated aqueous solution of sodium chloride and dried over anhydrous sodium sulfate. The solvent was distilled at reduced pressure. The residue was subjected to silica gel column chromatography using benzene-ethyl acetate (20:1) to separate and purify the contemplated product, giving 105 mg of benzyl ester of 2-allyloxy-7-phenoxyacetamido-3-desacetoxy cephalosporanic acid in 80% yield. The IR and $^1$HNMR spectrum data of the product were thoroughly identical with those of the product obtained in Example 1.

EXAMPLES 3 TO 20

The same procedure as Example 1 was repeated with the exception of using the ester of 2-acetoxy-3-desacetoxy cephalosporanic acid, nucleophilic reagents and acid catalysts as listed in Table I below. Table II shows the IR and $^1$HNMR spectrum data of the products obtained.

TABLE I

| Ex. | Compound (I) R¹ R² (mmol) | YH (mmol) | Acid catalyst (mmol) | Solvent (ml) | Temperature (°C.) | Time (min.) | Compound (II) Yield (%) |
|---|---|---|---|---|---|---|---|
| 3 | PhOCH$_2$ PhCH$_2$ (0.35) | [3-methylthiophene-like diene] (31) | TiCl$_4$ (0.82) | CH$_2$Cl$_2$ (7.5) | −30 | 10 | 95 |
| 4 | PhOCH$_2$ PhCH$_2$ (0.35) | (31) | TiCl$_4$ (0.82) | CHCl$_3$ (7.5) | −30 | 15 | 90 |
| 5 | PhOCH$_2$ PhCH$_2$ (0.35) | (31) | TiCl$_4$ (0.82) | CH$_2$Cl$_2$ (7.5) | −30 | 15 | 90 |
| 6 | PhOCH$_2$ PhCH$_2$ (0.70) | [3-methylfuran] (50.4) | p-TsOH (0.06) | CH$_2$Cl$_2$ (0.5) CH$_3$CN (0.5) | −5∼0 | 480 | 85 |
| 7 | PhOCH$_2$ PhCH$_2$ (0.69) | (50.0) | TiCl$_4$ (0.073) | CH$_2$Cl$_2$ (10.0) | −25∼−15 | 240 | 87 |
| 8 | PhOCH$_2$ PhCH$_2$ (0.35) | [N-methyl pyrrole] (0.5) | AlCl$_3$ (0.5) | CH$_2$Cl$_2$ (10.0) | −30∼−20 | 100 | 91 |
| 9 | PhOCH$_2$ PhCH$_2$ (0.37) | [1-phenyl-1H-tetrazole-5-thiol] (0.51) | AlCl$_3$ (0.49) | CH$_2$Cl$_2$ (7.5) | −35∼−18 | 66 | 90 |
| 10 | PhOCH$_2$ PhCH$_2$ (0.35) | [1-phenyl-1H-tetrazole-5-thiol] (0.50) | AlCl$_3$ (0.50) | CHCl$_3$ (7.5) | −35∼−25 | 90 | 88 |

TABLE I-continued $$\underset{(I)}{\underset{\underset{CO_2R^2}{|}}{R^1CONH-\!\!\!\begin{array}{c}S\\ \square\\ N\end{array}\!\!\!-CH(OAc)CH_3}} \xrightarrow[\text{Acid catalyst}]{YH} \underset{(II)}{\underset{\underset{CO_2R^2}{|}}{R^1CONH-\!\!\!\begin{array}{c}S\\ \square\\ N\end{array}\!\!\!-CH(Y)CH_3}}$$

| Ex. | Compound (I) $R^1$ $R^2$ (mmol) | YH (mmol) | Acid catalyst (mmol) | Solvent (ml) | Temperature (°C.) | Time (min.) | Compound (II) Yield (%) |
|---|---|---|---|---|---|---|---|
| 11 | $PhOCH_2$  $PhCH_2$ (0.35) | 1-methyl-1H-tetrazole-5-thiol (0.53) | $AlCl_3$ (0.46) | $CH_2Cl_2$ (7.0) | $-30 \sim -20$ | 120 | 83 |
| 12 | $PhOCH_2$  $PhCH_2$ (0.35) | 5-methyl-2-(methylthio)-1,3,4-thiadiazole-... -thiol (0.48) | $AlCl_3$ (0.48) | $CH_2Cl_2$ (7.0) | $-24 \sim -18$ | 120 | 80 |
| 13 | $PhOCH_2$  $PhCH_2$ (0.59) | HOOC-CH$_2$CH$_2$-SH (0.88) | $TiCl_4$ (0.18) | $CH_2Cl_2$ (5.0) | $-30 \sim -10$ | 180 | 75 |
| 14 | $PhOCH_2$  $PhCH_2$ (0.60) | $CH_3CH_2CH_2CH_2$-SH (0.92) | $TiCl_4$ (0.18) | $CH_2Cl_2$ (5.0) | $-40 \sim -30$ | 180 | 68 |
| 15 | $PhOCH_2$  $CH_3$ (0.30) | 2-methylfuran (2.0) | $TiCl_4$ (0.20) | $CH_2Cl_2$ (5.0) | $-30 \sim -15$ | 180 | 91 |
| 16 | $PhCH_2$  $CH_3$ (0.20) | 2-methylfuran (10.0) | $TiCl_4$ (0.10) | $CH_2Cl_2$ (4) | $-30 \sim -15$ | 180 | 88 |
| 17 | $PhCH_2$  $PhCH_2$ (0.25) | 2-methylfuran (11.0) | $TiCl_4$ (0.15) | $CH_2Cl_2$ (5) | $-30 \sim -15$ | 180 | 83 |
| 18 | Ph   $CH_3$ (0.15) | 2-methylfuran (8.0) | $TiCl_4$ (0.11) | $CH_2Cl_2$ (5) | $-30 \sim -15$ | 180 | 85 |
| 19 | $PhOCH_2$  $CH_3$ (0.30) | $CH_3OH$ (30 ml) | $I_2$ (5 mg) | — | r.t. | 120 | 98 |
| 20 | $PhOCH_2$  $PhCH_2$ (0.32) | $CH_3OH$ (30 ml) | $I_2$ (5 mg) | — | r.t. | 120 | 99 |

TABLE II

| Ex. | Compound (II) R¹ | R² | Y | IR (CHCl$_3$, cm$^{-1}$), $^1$HNMR (CDCl$_3$, δ, ppm) |
|---|---|---|---|---|
| 3 | PhOCH$_2$ | PhCH$_2$ | CH$_3$—〈S〉— (2,5-disubstituted thiophene) | IR: 1783, 1725, 1693<br>NMR: 2.14 (s, 3H), 2.44 (s, 3H), 4.54 (s, 2H),<br>4.26 (s, 1H), 4.95 (d, 1H, 5.2Hz),<br>5.32 (s, 2H), 5.94 (dd, 1H, 5.2Hz, 8.0Hz),<br>6.55 (s, 2H), 6.78–7.26 (m, 11H) |
| 4 | | | | same as above |
| 5 | | | | same as above |
| 6 | PhOCH$_2$ | PhCH$_2$ | CH$_3$—〈O〉— (2,5-disubstituted furan) | IR: 1782, 1724, 1698<br>NMR: 2.12 (s, 3H), 2.28 (s, 3H), 4.57 (s, 2H),<br>4.61 (s, 1H), 5.10 (d, 1H, 5Hz),<br>5.35 (s, 2H), 5.90 (dd, 1H, 5Hz, 8.4Hz),<br>5.98 (s, 2H), 6.9–7.7 (m, 11H) |
| 7 | | | | same as above |
| 8 | PhOCH$_2$ | PhCH$_2$ | N-methylpyrrole-2,5-diyl | IR: 1784, 1725, 1698<br>NMR: 2.07 (s, 3H), 3.60 (s, 3H), 4.50 (s, 2H),<br>4.54 (s, 1H), 4.80 (d, 1H, 5Hz), 5.29 (s, 2H),<br>5.6–6.05 (m, 3H), 6.5–7.6 (m, 13H) |
| 9 | PhOCH$_2$ | PhCH$_2$ | 1-phenyl-1,2,3,4-tetrazol-5-yl-thio (N=N/N–N/Ph) —S— | IR: 1795, 1735, 1700<br>NMR: 2.22 (s, 3H), 4.51 (s, 2H)<br>5.06 (d, 1H, 4.2Hz), 5.24 (s, 2H),<br>5.87 (dd, 1H, 4.2Hz, 8.8Hz),<br>6.7–7.7 (m, 16H) |
| 10 | | | | same as above |
| 11 | PhOCH$_2$ | PhCH$_2$ | 1-methyl-1,2,3,4-tetrazol-5-yl-thio | IR: 1785, 1723, 1692<br>NMR: 2.26 (s, 3H), 3.90 (s, 3H), 4.48 (s, 2H),<br>5.23 (d, 1H, 5Hz), 5.24 (s, 2H),<br>5.71 (s, 1H), 5.93 (dd, 1H, 5Hz, 8Hz),<br>6.7–7.5 (m, 1H) |
| 12 | PhOCH$_2$ | PhCH$_2$ | 5-methyl-1,3,4-thiadiazol-2-yl-thio | IR: 1790, 1730, 1698<br>NMR: 2.30 (s, 3H), 2.78 (s, 3H), 4.58 (s, 2H),<br>5.34 (d, 1H, 4.4Hz), 5.35 (s, 2H),<br>5.81 (s, 1H), 6.05 (dd, 1H, 4.4Hz, 9.6Hz),<br>6.7–7.6 (m, 11H) |
| 13 | PhOCH$_2$ | PhCH$_2$ | HOOC–CH$_2$CH$_2$–S— | IR: 1780, 1710, 1690<br>NMR: 2.18 (s, 3H), 2.5–3.1 (m, 4H), 4.54 (s, 3H),<br>5.25 (s, 2H), 5.32 (d, 1H, 5Hz),<br>5.95 (dd, 1H, 5Hz, 9Hz), 6.7–8.6 (m, 11H) |
| 14 | PhOCH$_2$ | PhCH$_2$ | n-butyl-S— | IR: 1780, 1720, 1695<br>NMR: 0.9 (s, 3H), 1.55 (m, 4H), 2.22 (s, 3H),<br>2.74 (m, 2H), 4.45 (s, 1H), 4.49 (s, 2H),<br>5.30 (s, 2H), 5.39 (d, 1H, 5Hz),<br>6.00 (dd, 1H, 5Hz, 10Hz), 6.8–7.6 (m, 11H) |
| 15 | PhOCH$_2$ | CH$_3$ | CH$_3$—〈O〉— | IR: 1780, 1730, 1690<br>NMR: 2.13 (s, 3H), 2.26 (s, 3H), 3.82 (s, 3H),<br>4.52 (s, 2H), 4.60 (s, 1H), 5.08 (d, 1H, 5Hz),<br>5.91 (dd, 1H, 5Hz, 8Hz), 5.98 (bs, 2H),<br>6.8–7.7 (m, 6H) |
| 16 | PhCH$_2$ | CH$_3$ | CH$_3$—〈O〉— | IR: 1782, 1732, 1697<br>NMR: 2.06 (s, 3H), 2.29 (s, 3H), 3.56 (s, 2H),<br>3.84 (s, 3H), 4.57 (s, 1H),<br>4.99 (d, 1H, 5Hz), 5.78 (dd, 1H, 5Hz, 9Hz),<br>6.60 (d, 1H, 9Hz), 5.99 (bs, 2H), 7.27 (s, 5H) |
| 17 | PhCH$_2$ | PhCH$_2$ | CH$_3$—〈O〉— | IR: 1783, 1725, 1690<br>NMR: 2.08 (s, 3H), 2.27 (s, 3H), 3.60 (s, 2H),<br>4.60 (s, 1H), 5.00 (d, 1H, 5Hz), 5.33 (s, 2H),<br>5.80 (dd, 1H, 5Hz, 9Hz), 5.97 (bs, 2H),<br>6.70 (d, 1H, 9Hz), 7.28 (s, 5H), 7.30 (s, 5H) |

TABLE II-continued

| Ex. | Compound (II) R¹ | R² | Y | IR (CHCl₃, cm⁻¹), ¹HNMR (CDCl₃, δ, ppm) |
|---|---|---|---|---|
| 18 | Ph | $CH_3$ | 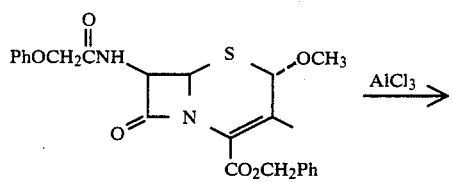 | IR: 1785, 1733, 1685<br>NMR: 2.05 (s, 3H), 2.28 (s, 3H), 3.85 (s, 3H),<br>4.66 (s, 1H), 5.10 (d, 1H, 5Hz),<br>5.85 (dd, 1H, 5Hz, 9Hz), 6.00 (bs, 2H),<br>6.50 (d, 1H, 9Hz), 6.7–7.7 (m, 5H) |
| 19 | $PhOCH_2$ | $CH_3$ | ⤴$OCH_3$ | IR: 1787, 1729, 1692<br>NMR: 2.14 (s, 3H), 3.42 (s, 3H), 3.82 (s, 3H),<br>4.54 (s, 2H), 4.77 (s, 1H),<br>5.05 (d, 1H, 4.8Hz), 5.88 (dd, 1H, 4.8Hz, 9Hz),<br>6.77–7.62 (m, 6H) |
| 20 | $PhOCH_2$ | $PhCH_2$ | ⤴$OCH_3$ | IR: 1780, 1730, 1688<br>NMR: 2.14 (s, 3H), 3.41 (s, 3H), 4.54 (s, 2H),<br>4.74 (s, 1H), 5.02 (d, 1H, 4.8Hz),<br>5.24 (s, 2H), 5.86 (dd, 1H, 4.8Hz, 10Hz),<br>6.7–7.5 (m, 11H) |

EXAMPLE 21

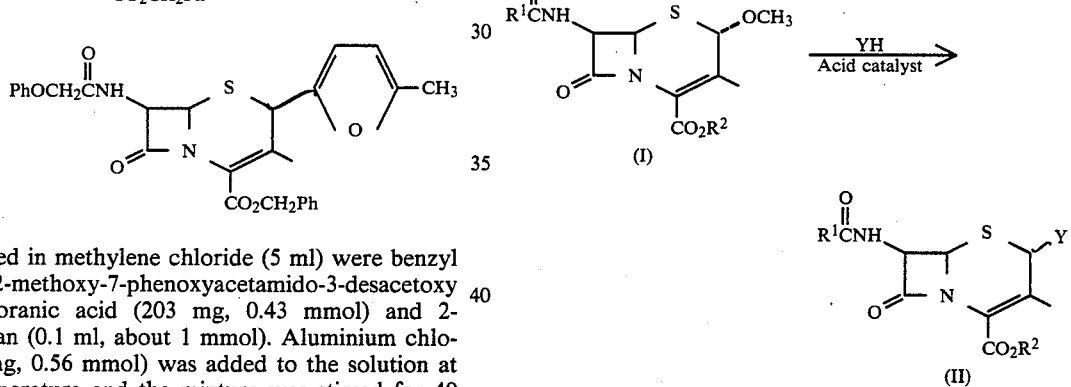

Dissolved in methylene chloride (5 ml) were benzyl ester of 2-methoxy-7-phenoxyacetamido-3-desacetoxy cephalosporanic acid (203 mg, 0.43 mmol) and 2-methylfuran (0.1 ml, about 1 mmol). Aluminium chloride (74 mg, 0.56 mmol) was added to the solution at room temperature and the mixture was stirred for 40 minutes. An aqueous solution of sodium hydrogen carbonate was added to the reaction mixture and the mixture was extracted with methylene chloride. The extract was washed with a saturated aqueous solution of sodium chloride, dried over anhydrous sodium sulfate and concentrated. The residue was subjected to silica gel column chromatography using benzene-ethyl acetate (10:1), to separate and purify the contemplated product, giving 149 mg of benzyl ester of 2-(2-methyl-5-furyl)-7-phenoxyacetamido-3-desacetoxy cephalosporanic acid in 82% yield. The IR and ¹HNMR spectrum data of the products thus purified were totally identical with those of the product obtained in Example 6.

EXAMPLES 22 TO 26

The procedure of Example 21 was followed except that use was made of the ester of 2-methoxy-3-desacetoxy cephalosporanic acid and nucleophilic reagents as indicated in Table III below. Table IV shows the IR and ¹HNMR spectrum data of the products obtained.

TABLE III

| Ex. | Compound (I) R¹ R² (mmol) | YH (mmol) | Acid catalyst (mmol) | Solvent (ml) | Temperature (°C.) | Time (min.) | Compound (II) Yield (%) |
|---|---|---|---|---|---|---|---|
| 22 | $PhOCH_2$  $PhCH_2$ (1.00) | $CH_3$—furyl—H (40) | p-TsOH (0.11) | $CH_2Cl_2$ (2) | r.t. | 3 | 88 |
| 23 | $PhOCH_2$  $PhCH_2$ (0.65) | furyl—H (4 ml) | p-TsOH (0.12) | — | r.t. | 5 | 70 |

TABLE III-continued

| | Compound (I) | | | Acid | | | | Compound |
| Ex. | R¹ (mmol) | R² | YH (mmol) | catalyst (mmol) | Solvent (ml) | Temperature (°C.) | Time (min.) | (II) Yield (%) |
| --- | --- | --- | --- | --- | --- | --- | --- | --- |
| 24 | PhOCH₂ (0.80) | CH₃ | CH₃—〈O〉—H (30) | p-TsOH (0.10) | AcOEt (2) | r.t. | 6 | 72 |
| 25 | PhCH₂ (0.95) | PhCH₂ | CH₃—〈O〉—H (42) | p-TsOH (0.15) | AcOEt (2) | r.t. | 5 | 63 |
| 26 | PhCH₂ (1.10) | CH₃ | CH₃—〈O〉—H (33) | p-TsOH (0.20) | HCOOEt (2) | r.t. | 7 | 69 |

TABLE IV

| | Compound (II) | | | |
| Ex. | R¹ | R² | Y | IR (CHCl₃, cm⁻¹), ¹HNMR (CDCl₃, , ppm) |
| --- | --- | --- | --- | --- |
| 22 | PhOCH₂ | PhCH₂ | 〈O〉—CH₃ | Same as Example 6 |
| 23 | PhOCH₂ | PhCH₂ | 〈O〉 | IR: 1787, 1730, 1697<br>NMR: 2.08 (s, 3H), 4.49 (s, 2H), 4.58 (s, 1H),<br>5.01 (d, 1H, 5Hz), 5.28 (s, 2H),<br>5.88 (dd, 1H, 5Hz, 9Hz), 5.95–6.40 (m, 2H),<br>6.7–7.6 (m, 12H) |
| 24 | PhOCH₂ | CH₃ | 〈O〉—CH₃ | Same as Example 15 |
| 25 | PhCH₂ | PhCH₂ | 〈O〉—CH₃ | Same as Example 17 |
| 26 | PhCH₂ | CH₃ | 〈O〉—CH₃ | Same as Example 16 |

We claim:

1. A compound represented by the formula:

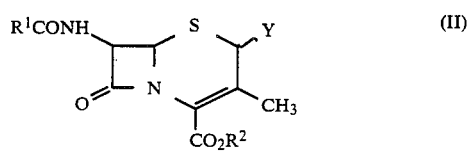

(II)

wherein R¹ represents phenyl; phenyl substituted with lower alkyl, lower alkoxy, halogen or nitro; phenylmethyl; phenylmethyl substituted with lower alkyl, lower alkoxy, halogen or nitro on the benzene nucleus; phenoxymethyl; or phenoxymethyl substituted with lower alkyl, lower alkoxy, halogen or nitro on the benzene nucleus: R² represents hydrogen atom or protective group for carboxylic acid: and Y represents carboxyalkylthio group or group of the formula:

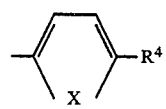

wherein R⁴ represents hydrogen atom or lower alkyl group and X represents —O—, —S— or >N—CH₃.

2. A compound as defined in claim 1 in which R¹ is phenyl group, phenylmethyl group or phenoxymethyl group.

3. A compound as defined in claim 1 or 2 in which R² is phenyl-substituted methyl group or alkyl group.

* * * * *